United States Patent [19]

Lien et al.

[11] Patent Number: 4,504,629

[45] Date of Patent: Mar. 12, 1985

[54] POLYMERS WITH GRAFT α-ALKYLACRYLATE FUNCTIONALITY

[75] Inventors: Samuel Q. S. Lien, South Windsor, now by change of name from Qcheng S. Lien; Steven T. Nakos, East Hartford, both of Conn.

[73] Assignee: Loctite Corporation, Newington, Conn.

[21] Appl. No.: 515,702

[22] Filed: Jul. 20, 1983

[51] Int. Cl.³ .................................................. C08F 275/00
[52] U.S. Cl. .................................... 525/288; 525/193; 525/284; 525/478; 525/479
[58] Field of Search ............... 525/288, 193, 284, 478, 525/479

[56] References Cited

U.S. PATENT DOCUMENTS

| | | |
|---|---|---|
| 2,793,223 | 5/1957 | Merker . |
| 2,922,806 | 1/1960 | Merker . |
| 2,956,044 | 10/1960 | Merker . |
| 3,417,161 | 12/1968 | Douds et al. . |
| 3,577,264 | 5/1971 | Nordstrom . |
| 3,878,263 | 4/1975 | Martin . |
| 4,035,355 | 7/1977 | Baney . |
| 4,139,519 | 2/1979 | Itoh et al. . |
| 4,295,909 | 10/1981 | Baccei . |
| 4,309,526 | 1/1982 | Baccei . |
| 4,348,454 | 9/1982 | Eckberg . |

FOREIGN PATENT DOCUMENTS 1323869 of 0000 United Kingdom .
1384898 of 0000 United Kingdom .

*Primary Examiner*—Melvyn I. Marquis
*Attorney, Agent, or Firm*—Walter J. Steinkraus; Eugene F. Miller

[57] ABSTRACT

Polymers having α-alkylacrylate functionality may be prepared by hydrosilating an aliphatically unsaturated polymer with a grafting agent of structure (A) or (B):

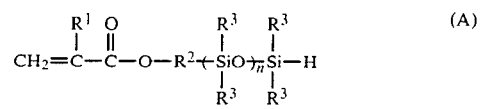

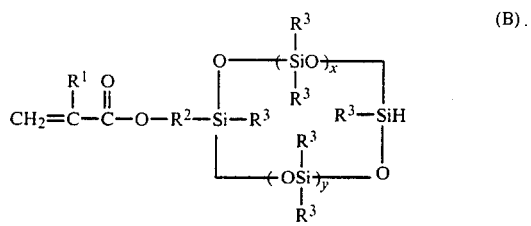

where $R^1$ is an alkyl group; $R^2$ is a divalent group nonreactive under hydrosilation conditions; n is 0, 1, 2, 3, or 4; x and y are 0, 1, 2, 3 or 4 and $x+y=1, 2, 3$ or 4; and, the $R^3$ groups are the same or different alkyl, substituted alkyl, aryl, substituted aryl or

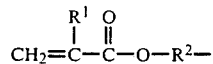

groups.

Preferred olefinically unsaturated polymers include homopolymers and copolymers of butadiene or alkyl substituted butadiene and polyorganosiloxanes with unsaturated hydrocarbyl groups such as vinyl or allyl.

16 Claims, No Drawings

POLYMERS WITH GRAFT α-ALKYLACRYLATE FUNCTIONALITY

BACKGROUND OF THE INVENTION

Polymers with acrylic (acrylate, methacrylate, etc.) functionality are desirable because of the ease in which such polymers undergo free radical initiated additions which crosslink the resin or further polymerize it with unsaturated monomers. Among the well known applications of such polymers are anaerobic, UV, and two-component chemically cured adhesive systems as well as various coatings.

An especially desirable class of polymers in which grafted acrylic functionality is advantageous is the polyorganosiloxane group, commonly known as silicones. Silicone resins are well known for the desirable thermal, electrical and weather resistant properties.

In U.S. Pat. No. 3,577,264 to Nordstrom, there is described a radiation curable film forming paint formulation which employs a solution of vinyl monomers and an alpha-beta olefinically unsaturated siloxane formed by condensing a hydroxy acrylic ester with a siloxane having hydroxy or hydrocarbonoxy groups. The acrylate functionality is bound to the siloxane by a Si—O—C bond.

In U.S. Pat. No. 3,878,263 to Martin, there are described acrylate-functional polyorganosiloxanes which are prepared from acrylate or methacrylate functional silanes by equilibration with organopolysiloxanes. The methacrylate functional silanes reportedly may be prepared by hydrosilation of an acrylate or methacrylate ester of an unsaturated alcohol or by reaction of an appropriate chloroalkylsilane with a tertiary amine salt of acrylic or methacrylic acid.

In U.S. Pat. No. 4,035,355 to Baney et al., there are described anaerobically curing compositions which employ polysiloxane polymers in which acrylate groups are bonded to the polymer backbone by Si—C bonds. These polymers are also produced from organosilanes having both acrylate functionality and hydrolyzable functionality by equilibration. Other references relating to acrylate functional silicones include U.S. Pat. Nos. 2,793,223, 2,922,806, 2,956,044, 3,417,161 and 4,348,454 and U.K. Pat. Nos. 1323869 and 1384898.

Examples of other acrylic functional polymers include urethane-acrylate capped prepolymers as disclosed in U.S. Pat. Nos. 4,295,909 and 4,309,526 to Baccei, and the commercially available polyethylene glycol dimethacrylate (PEGMA). A commercially available butadiene polymer with terminal methacrylate groups is B. F. Goodrich VTBN.

In U.S. Pat. No. 4,139,519 there is described a method of grafting organosilicon groups, such as trimethylsiloxy or (trimethylsiloxy)dimethylsiloxy groups to butadiene polymers and copolymers to improve their viscosity and curing properties. The method involves hydrosilation of the butadiene double bonds with a SiH functional silane or siloxane.

SUMMARY OF THE INVENTION

The present invention encompasses novel graft polymers which are the reaction product of a silicon hydride functional grafting agent having at least one α-alkylacrylate group attached thereto and an aliphatically unsaturated polymer. The invention further includes the novel silicon hydride functional grafting agents utilized in the preparation of the inventive polymers. A further aspect of the invention is the method of adding α-alkylacrylate functionality to an aliphatically unsaturated polymer by hydrosilating the polymer in the presence of a hydrosilation catalyst with the grafting agents of the invention.

The inventive process enables the polymers with relatively unreactive unsaturation to acquire very reactive methacrylate functionalities. Therefore, these polymers can be cured or cocured with other vinyl monomers under less severe conditions using UV, peroxide, anaerobic or other radical curing systems. When formulated with appropriate initiator systems, the inventive polymers can be self-cured (vulcanized) or can be cured with other ethylenically unsaturated monomers to give graft copolymers with entirely new properties. Uncured formulations of elastomeric backbone polymers with ethylenic monomers, such as polyether dimethacrylate monomers, are useful as adhesives and coatings giving a cured product which is flexible and tough.

Unlike terminally methacrylated rubbers, the invention permits the amount of methacrylate or other α-alkylacrylate functionality per molecule to be varied over a wide range to achieve desired crosslink density and cure speed.

The invention is especially useful in the synthesis of methacrylated silicones because it produces the desired product in high yield from materials which are readily available commercially.

DETAILED DESCRIPTION OF THE INVENTION

The grafting agents of the invention are selected from compounds of formula (A) or (B) and mixtures thereof.

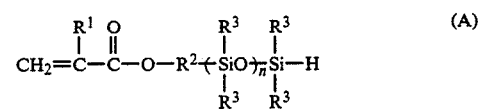

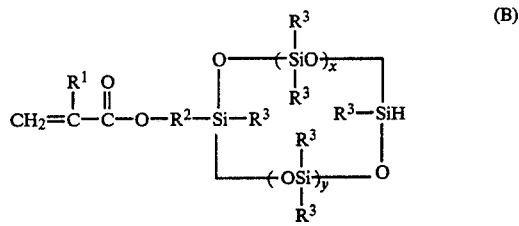

where $R^1$ is an alkyl group; $R^2$ is a divalent group nonreactive under hydrosilation reaction conditions; n is 0, 1, 2, 3, or 4; x and y are 0–4 and $x+y=1-4$; and the $R^3$ groups are the same or different alkyl, substituted alkyl, aryl, substituted aryl or

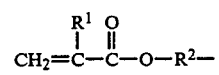

groups. Preferably $R^1$ is methyl. Examples of $R^2$ groups are alkyleneoxy, polyalkyleneoxy, alkylene, alkyleneoxyalkylene, arylene, alkylarylene, arylakylene or alkenylene.

Where $R^1$ is alkyleneoxy or polyalkyleneoxy, the grafting agent may be prepared by the condensation reaction between chlorosilanes or siloxanes and a hydroxy-terminated α-alkylacrylate. The synthesis is exemplified in Examples 1 and 2 by the reaction of hydroxypropyl methacrylate with dimethylchlorosilane and methyldichlorosilane, respectively.

EXAMPLE 1

A solution of hydroxypropylmethacrylate (36.0 g) and 22.1 g pyridine was added dropwise with stirring to a solution of 26.5 g dimethylchlorosilane in 50 ml hexane under a dry nitrogen blanket. After addition was complete and the exotherm had subsided, the mixture was filtered to remove pyridine hydrochloride which was washed with hexane and refiltered. The combined filtrates were stripped to remove hexane. Phenothiazine was added to the crude product which was then vacuum distilled. The purified product, boiling at 60°-62° C. and 2.5 mmHg, was obtained in 71% yield (35.8 g). NMR and IR were consistent with a mixture of compounds represented by formulas (C) and (C').

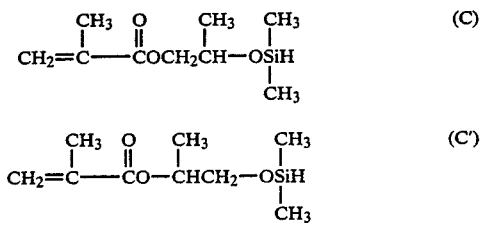

EXAMPLE 2

Methyldichlorosilane (79.4 g) was added dropwise with ice bath cooling and mechanical stirring to 200.0 g hydroxypropylmethacrylate 109.0 g pyridine and 1.4 g hydroquinone monomethyl ether in 400 ml hexane. A nitrogen blanket was maintained over the reaction mixture. The temperature was maintained below 30° C. and stirring was continued for 2 hrs. at room temperature after addition was completed. Pyridine hydrochloride was filtered off and washed as in Example 1 after which the combined filtrates were stripped in a rotary evaporator. Deep stripping at 65° C. and 0.2 mmHg gave a crude product which was stirred overnight with 4 g activated alumina. The alumina was then filtered off to give 202.4 g of a water white product, corresponding to an 89% yield. NMR was consistent with the assigned structure of formula (D).

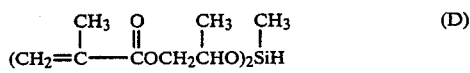

The method of preparing the novel methacrylated polymers of the invention is the hydrosilation of an olefinically unsaturated polymer with a grafting agent in accordance with the invention. The reactions are carried out with a catalyst. The hydrosilation catalysts are well known to those skilled in the art. Examples are platinum, chloroplatinic acid, hydrocarbon-platinum complexes, rhodium complexes, etc. Platinum-based catalysts are preferred at levels of between 10 ppm to 500 ppm platinum, preferably between 50 ppm and 300 ppm.

The reaction temperatures may vary from about 0° C. to about 100° C. depending on the reactivity of the polymeric substrate and the concentration and types of catalyst used. Temperatures above 100° C. should typically be avoided since the methacrylate groups will tend to thermally polymerize even in the presence of an added inhibitor.

The reactions can be carried out neat or in organic solvents which do not interfere with the hydrosilation. Examples of such solvents are toluene, hexane, tetrahydrofuran, methylenedichloride, benzene, etc. The reaction may be followed easily by the disappearance of the SiH absorption peak at 2200 cm$^{-1}$ of the infrared spectrum.

Examples 3-5 describe the methacrylation of butadiene or isoprene polymers or copolymers using the grafting agents of Examples 1 or 2. Examples 6 and 7 exemplify some cured formulations prepared from a product prepared as in Example 3.

EXAMPLE 3

10.1 g of the product of Example 1, 50.0 g of Butarez-NF, a polybutadiene having a molecular weight of 16000, 10%, 1,2 addition, and sold by Phillips Petroleum Co., and 2.0 g of 1% chloroplatinic acid in butylacetate were mixed in 100 ml toluene and heated to 70° C. for 4 hrs. IR showed no evidence of SiH. The clear solution was then stripped to remove solvent and deep-stripped for two hrs. at 70° C. and 0.2 mmHg to give 59.0 g of light yellow product.

EXAMPLE 4

100 g of Kraton 1107, a styrene-isoprene-styrene block copolyer sold by Shell Chemical Co. and containing 85.45% isoprene, was dissolved in 300 ml toluene forming a viscous solution. 3.38 g of a grafting agent prepared as in Example 1 was added followed by 2.5 g of 2% chloroplatinic acid in butyl acetate. After 3 hrs. at 70° C. the SiH stretch had disappeared in the IR and the reaction was allowed to cool. The cooled mixture was poured into 1 liter acetone with rapid stirring to obtain the product as a crumb. Filtration through a course fritted funnel gave a grey product which was dried overnight at 40° C. in a vacuum oven. Yield was 77.4 g.

EXAMPLE 5

100 g Kraton 1101, a styrene-butadiene-styrene block copolymer sold by Shell Chemical Co. containing 68.8 weight% polybutadiene, was dissolved over 3 hrs. in 300 ml toluene. 13.97 g of the product of Example 2 and 1.0 g 2% chloroplatinic acid were then added and the mixture heated under nitrogen to 70° C. After 6 hrs. IR showed no residual SiH and the solution was allowed to cool to room temperature. The solution was then slowly poured into rapidly stirred acetone and the ppt collected on a paperless Buchner funnel. The sticky grainy polymer was dried overnight at 50° C. in a vacuum oven producing 96.3 g of a nearly colorless spongy block.

EXAMPLE 6

A methacrylated butadiene X, prepared as in Example 3 and having a theoretical 16 methacrylate units per molecule, was formulated in curable compositions as set forth in Table I, the entries representing parts by weight.

TABLE I

| ingredients/formulation no. | 1 | 2 | 3 | 4 |
|---|---|---|---|---|
| Polymer X | 50 | 60 | 70 | 60 |
| isobornyl | 36 | 26 | 16 | 21 |

TABLE I-continued

| ingredients/formulation no. | 1 | 2 | 3 | 4 |
|---|---|---|---|---|
| methacrylate ethoxylated bisphenol-A dimethacrylate | 5 | 5 | 5 | 10 |
| Aerosil 200 | 3 | 3 | 3 | 3 |
| methacrylic acid | 4.5 | 4.5 | 4.5 | 4.5 |
| t-butyl perbenzoate | 1 | 1 | 1 | 1 |
| saccharin | 0.5 | 0.5 | 0.5 | 0.5 |

Aerosil 200 is a fumed silica sold by Degussa.

The formulations of Table I were applied at 0, 20 and 40 mil gaps to 1" sandblasted steel laps and impact blocks, which had been primed with an adhesive primer sold by Loctite Corporation under the number 785-45 and cured for 1 hr. in a 200° F. oven. Tensile shear was determined per ASTM D-1002 (modified for the 20 and 40 mil gap specimens by assembling the laps with wire shims). Impact values were run per ASTM D-950. The results, averages of 4 specimens, are listed in Table II.

TABLE II

| Formulation Gap | Average Tensile Shear (Psi) | Average Impact (Psi) |
|---|---|---|
| 1-0 | 1120 | 2.0 |
| 1-20 | 1228 | 5.4 |
| 1-40 | 1270 | 9.6 |
| 2-0 | 828 | 1.6 |
| 2-20 | 669 | 4.2 |
| 2-40 | 614 | 7.0 |
| 3-0 | 586 | 1.4 |
| 3-20 | 362 | 3.8 |
| 3-40 | 304 | 5.0 |
| 4-0 | 806 | 1.7 |
| 4-20 | 732 | 4.6 |
| 4-40 | 618 | 6.7 |

EXAMPLE 7

A sample of methacrylated butadiene polymer A, described in the previous example was mixed with 2% by weight diethoxyacetophenone and poured into a depth of ¼" into a 50 ml polyethylene beaker. The beaker was placed in a UV chamber and exposed to 60 mw/cm UV light for 20 sec., after which it was inverted and irradiated for an additional 20 sec. The sample had cured to a disk having a soft rubbery consistency. The cured disk retained substantial flexibility when chilled to −44° C. for 1 hr.

Where $R^2$ of the grafting agent of formula A is alkyleneoxy or polyalkyleneoxy some of the C—O—Si bond contained therein is subject to hydrolysis when the grafting agent or a graft polymer thereof is exposed to excessive moisture. It is therefore preferred that the grafting agents not contain a C—O—Si linkage, such as when $R^2$ is alkylene, alkyleneoxyalkylene, arylene, alkenylene, alkylarylene or arylalkylene. Examples are propylene, ethyleneoxypropylene, phenylene, propylenephenylene, phenylenemethylene, etc. One method of synthesis of such compounds is the controlled hydrosilation of an unsaturated methacrylate such as allyl methacrylate, propargyl methacrylate or allyloxyethyl methacrylate with a dihydrosilane or dihydrodisiloxane. The reaction is conducted utilizing an excess of the dihydrosilicon compound and gradually adding the alkene methacrylate thereto so as to minimize dimer methacrylate production.

Another method of preparing siloxane grafting agents is exemplified by Example 8.

EXAMPLE 8

Distilled methacryloxypropyldimethylchlorosilane, prepared by hydrosilation of allyl methacrylate with dimethylchlorosilane was converted to the corresponding silanol by adding 25.00 gm of the methacryloxypropyldimethylchlorosilane dropwise at 5° C. to a rapidly stirring mixture of 50 ml water, 11.4 gm NaHCO₃, 100 ml benzene and 0.1 gm pyridine. The reaction mixture was stirred for 1 hr. after the addition and then the aqueous layer was separated off. The organic layer was washed with a 50 ml portion of water.

The silanol containing benzene layer was then placed in a 250 ml 3-necked flask with 23.7 g pyridine and cooled to 5° C. Dimethylchlorosilane (18.9 gm) was added dropwise with moisture protection while maintaining the temperature below 10° C. Following the addition the mixture was stirred for an additional hour at room temperature. The reaction was quenched with ethanol, stripped and deep-stripped on a rotary evaporator to give 21.3 g of a light-colored liquid. NMR analysis indicated that the product contained about 46% of the desired grafting agent identified by the structure:

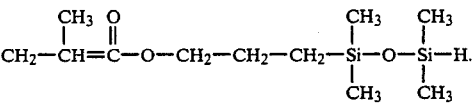

The inventive reaction is especially useful in the preparation of methacrylated silicones. Vinyl substituted silicones are preferred because of their ready commercial availability. However, silicones containing other alkenyl groups, such as allyl groups, may also be used in the invention. Unlike procedures which rely on equilibration polymerization techniques to prepare methacrylated silicones from methacrylated silanes, the inventive method may be used to prepare novel methacrylated silicones with molecular weights well in excess of the 40-50,000 maximum molecular weight obtainable by equilibration techniques. Example 9 demonstrates the preparation of a methacrylated silicone in accordance with the invention.

EXAMPLE 9

A vinyl terminated polydimethylsiloxane having an approximate molecular weight of 14,000 (0.144 meq vinyl/gm polymer) was hydrosilated with a grafting agent of the invention, using 25.0 g of the polymer, 2.18 g of the product of Example 8 and 0.5 g of a 2% solution of chloroplatinic acid in butyl acetate. The reactants were mixed with 50 ml benzene and heated to 70° C. for 2 hrs. under dry nitrogen. The reaction mixture was then cooled, and filtered through a diatomataceous earth filter aid. Approximately 0.01 g butylated hydroxytoluene was added and the mixture stripped to remove solvent and deep-stripped at 0.5 mmHg and 70° C. for 1 hr. to give 26.4 gm of a colorless product.

Methacrylation of the polymer was demonstrated by mixing 5 gm of the product with 2% diethoxyacetophenone and exposing the mixture in a 50 ml beaker to 70 mw/cm² UV irradiation for 1 min. per side. The product cured to a soft, tacky, rubber-like consistency.

We claim:

1. A method of adding α-alkylacrylate functionality to an aliphatically unsaturated polymer, the method comprising reacting at temperatures between about 0° C. and about 100° C. a grafting agent consisting essentially of a compound selected from (A), (B) and mixtures thereof with said aliphatically unsaturated polymer in the presence of a hydrosilation catalyst selected from platinum-based catalysts and rhodium complex catalysts, said grafting agent compounds (A) and (B) having the respective structures:

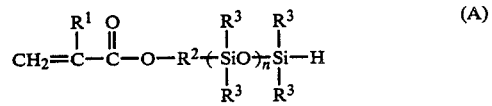
(A)

and

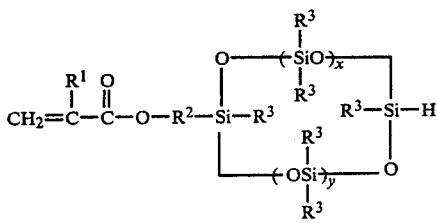

where $R^1$ is an alkyl group; $R^2$ is a divalent group nonreactive under hydrosilation conditions; n is 0, 1, 2, 3, or 4; x and y are 0, 1, 2, 3 or 4 and x+y=1, 2, 3 or 4; and, the $R^3$ groups are the same or different alkyl, substituted alkyl, aryl, substituted aryl or

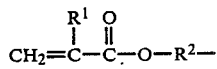

groups.

2. A method as in claim 1 wherein said catalyst is chloroplatinic acid.

3. A method as in claim 1 wherein $R^2$ is alkyleneoxy, polyalkyleneoxy, alkylene, alkyleneoxyalkylene, arylene, alkylarylene, arylalkylene, or alkenylene.

4. A method as in claim 4 wherein $R^2$ is propylene, propyleneoxy or ethyleneoxypropylene.

5. A method as in claim 1 wherein said unsaturated polymer is selected from homopolymers and copolymers of butadiene or alkyl-substituted butadienes.

6. A method as in claim 5 wherein said unsaturated polymer is selected from block copolymers of styrene and butadiene or styrene and isoprene.

7. A method as in claim 1 wherein said unsaturated polymer is polyorganosiloxane having a plurality of unsaturated hydrocarbyl groups.

8. A method as in claim 7 wherein said polyorganosiloxane unsaturated hydrocarbyl groups are allyl or vinyl groups.

9. A polymer comprising the hydrosilation reaction product of an aliphatically unsaturated polymer and a grafting agent consisting essentially of a compound of structure (A), (B), or mixtures thereof:

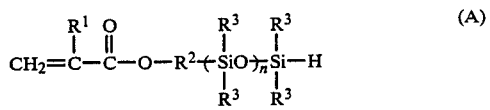
(A)

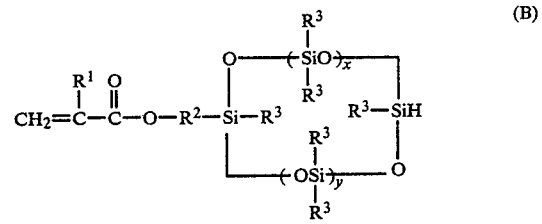
(B)

where $R^1$ is an alkyl group; $R^2$ is a divalent group nonreactive under hydrosilation reaction conditions; n is 0, 1, 2, 3, or 4; x and y are 0, 1, 2, 3 or 4 and x+y=1, 2, 3 or 4; and, the $R^3$ groups are the same or different alkyl, substituted alkyl, aryl, substitute aryl or

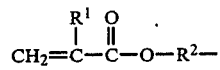

groups, said hydrosilation reaction being conducted in the presence of a platinum-based or rhodium complex hydrosilation catalyst at a temperature of between about 0° C. and about 100° C.

10. A polymer as in claim 9 wherein $R^1$ is methyl.

11. A polymer as in claim 9 wherein $R^2$ is alkyleneoxy, polyalkyleneoxy, alkylene, alkyleneoxyalkylene, arylene, alkylarylene or arylalkylene, or alkenylene.

12. A polymer as in claim 11 wherein $R^2$ is propylene, propyleneoxy or ethyleneoxypropylene.

13. A polymer as in claim 9 wherein said unsaturated polymer is selected from homopolymers and copolymers of butadiene or alkyl-substituted butadienes.

14. A polymer as in claim 13 wherein said unsaturated polymer is selected from block copolymers of styrene and butadiene or styrene and isoprene.

15. A polymer as in claim 9 wherein said unsaturated polymer is polyorganosiloxane having a plurality of unsaturated hydrocarbyl groups.

16. A polymer as in claim 15 wherein said polyorganosiloxane unsaturated hydrocarbyl groups are allyl or vinyl groups.

* * * * *